(12) United States Patent
Allen, IV et al.

(10) Patent No.: US 12,408,970 B2
(45) Date of Patent: Sep. 9, 2025

(54) SYSTEMS AND METHODS FOR SEALING AND DISSECTING TISSUE USING AN ELECTROSURGICAL FORCEPS INCLUDING A THERMAL CUTTING ELEMENT

(71) Applicant: Covidien LP, Mansfield, MA (US)

(72) Inventors: James D. Allen, IV, Broomfield, CO (US); John A. Hammerland, Arvada, CO (US); William E. Robinson, Boulder, CO (US); Daniel A Joseph, Golden, CO (US); Michael B. Lyons, Boulder, CO (US); Ken Netzel, Loveland, CO (US)

(73) Assignee: Covidien LP, Mansfield, MA (US)

( * ) Notice: Subject to any disclaimer, the term of this patent is extended or adjusted under 35 U.S.C. 154(b) by 402 days.

(21) Appl. No.: 16/838,551

(22) Filed: Apr. 2, 2020

(65) Prior Publication Data

US 2021/0307812 A1    Oct. 7, 2021

(51) Int. Cl.
*A61B 18/14* (2006.01)
*A61B 18/00* (2006.01)
*A61B 18/12* (2006.01)

(52) U.S. Cl.
CPC ...... *A61B 18/1445* (2013.01); *A61B 18/1233* (2013.01); *A61B 2018/00601* (2013.01); *A61B 2018/0063* (2013.01); *A61B 2018/00875* (2013.01); *A61B 2018/00898* (2013.01)

(58) Field of Classification Search
None
See application file for complete search history.

(56) References Cited

U.S. PATENT DOCUMENTS

| 2,068,721 A | 1/1937 | Frederick |
| 4,091,813 A | 5/1978 | Shaw et al. |
| D249,549 S | 9/1978 | Pike |

(Continued)

FOREIGN PATENT DOCUMENTS

| CN | 201299462 Y | 9/2009 |
| DE | 2415263 A1 | 10/1975 |

(Continued)

OTHER PUBLICATIONS

International Search Report mailed Jul. 2, 2021 and Written Opinion completed Jun. 23, 2021 corresponding to counterpart Int'l Patent Application PCT/US2021/020649.

*Primary Examiner* — Sean W Collins
*Assistant Examiner* — Nora W Rhodes

(57) ABSTRACT

A method for treating tissue includes determining whether tissue is present between first and second jaw members. In a case where it is determined that tissue is present between the first and second jaw members, the method further includes determining whether activation has been initiated. In a case where it is determined that activation has been initiated, the method further includes supplying electrosurgical energy to the first and second jaw members to seal the tissue and, if it is determined that sealing is complete: stopping the supply of electrosurgical energy; activating a thermal cutting element to supply thermal energy to cut the sealed present tissue; determining if thermal cutting is complete; and, in a case where it is determined that the thermal cutting is complete, stopping and the supply of thermal energy.

19 Claims, 5 Drawing Sheets

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,389,098 A | 2/1995 | Tsuruta et al. |
| 5,403,312 A | 4/1995 | Yates et al. |
| D358,887 S | 5/1995 | Feinberg |
| 5,465,895 A | 11/1995 | Knodel et al. |
| 5,480,409 A | 1/1996 | Riza |
| 5,582,611 A | 12/1996 | Tsuruta et al. |
| 5,582,617 A | 12/1996 | Klieman et al. |
| 5,647,869 A | 7/1997 | Goble et al. |
| D384,413 S | 9/1997 | Zlock et al. |
| 5,769,791 A | 6/1998 | Benaron et al. |
| H1745 H | 8/1998 | Paraschac |
| 5,810,811 A | 9/1998 | Yates et al. |
| 5,827,271 A | 10/1998 | Buysse et al. |
| 5,833,690 A | 11/1998 | Yates et al. |
| D402,028 S | 12/1998 | Grimm et al. |
| 5,876,401 A | 3/1999 | Schulze et al. |
| D408,018 S | 4/1999 | McNaughton |
| 5,891,142 A | 4/1999 | Eggers et al. |
| 5,911,719 A | 6/1999 | Eggers |
| D416,089 S | 11/1999 | Barton et al. |
| 6,024,741 A | 2/2000 | Williamson, IV et al. |
| D424,694 S | 5/2000 | Tetzlaff et al. |
| D425,201 S | 5/2000 | Tetzlaff et al. |
| 6,086,586 A | 7/2000 | Hooven |
| H1904 H | 10/2000 | Yates et al. |
| 6,270,497 B1 | 8/2001 | Sekino et al. |
| 6,273,887 B1 | 8/2001 | Yamauchi et al. |
| D449,886 S | 10/2001 | Tetzlaff et al. |
| 6,306,134 B1 | 10/2001 | Goble et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,402,747 B1 | 6/2002 | Lindemann et al. |
| H2037 H | 7/2002 | Yates et al. |
| D465,281 S | 11/2002 | Lang |
| D466,209 S | 11/2002 | Bon |
| 6,602,252 B2 | 8/2003 | Mollenauer |
| 6,736,813 B2 | 5/2004 | Yamauchi et al. |
| D493,888 S | 8/2004 | Reschke |
| 6,776,780 B2 | 8/2004 | Mulier et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,821,273 B2 | 11/2004 | Mollenauer |
| D502,994 S | 3/2005 | Blake, III |
| 6,860,880 B2 | 3/2005 | Treat et al. |
| 6,899,710 B2 | 5/2005 | Hooven |
| 6,929,641 B2 | 8/2005 | Goble et al. |
| D509,297 S | 9/2005 | Wells |
| 6,953,461 B2 | 10/2005 | McClurken et al. |
| 7,011,656 B2 | 3/2006 | McGaffigan et al. |
| 7,033,356 B2 | 4/2006 | Atterell et al. |
| D525,361 S | 7/2006 | Hushka |
| 7,070,597 B2 | 7/2006 | Truckai et al. |
| 7,083,619 B2 | 8/2006 | Truckai et al. |
| 7,112,201 B2 | 9/2006 | Truckai et al. |
| D531,311 S | 10/2006 | Guerra et al. |
| 7,125,409 B2 | 10/2006 | Truckai et al. |
| D533,274 S | 12/2006 | Visconti et al. |
| D533,942 S | 12/2006 | Kerr et al. |
| 7,147,637 B2 | 12/2006 | Goble |
| D535,027 S | 1/2007 | James et al. |
| 7,169,146 B2 | 1/2007 | Truckai et al. |
| D538,932 S | 3/2007 | Malik |
| D541,418 S | 4/2007 | Schechter et al. |
| 7,204,835 B2 | 4/2007 | Latterell et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| 7,270,664 B2 | 9/2007 | Johnson et al. |
| 7,276,068 B2 | 10/2007 | Johnson et al. |
| 7,326,202 B2 | 2/2008 | McGaffigan |
| 7,329,255 B2 | 2/2008 | McGaffigan |
| D564,662 S | 3/2008 | Moses et al. |
| D567,943 S | 4/2008 | Moses et al. |
| 7,354,440 B2 | 4/2008 | Truckal et al. |
| 7,357,802 B2 | 4/2008 | Palanker et al. |
| 7,364,577 B2 | 4/2008 | Wham et al. |
| 7,396,356 B2 | 7/2008 | Mollenauer |
| D575,395 S | 8/2008 | Hushka |
| D575,401 S | 8/2008 | Hixson et al. |
| 7,419,490 B2 | 9/2008 | Falkenstein et al. |
| D582,038 S | 12/2008 | Swoyer et al. |
| 7,686,827 B2 | 3/2010 | Hushka |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,815,641 B2 | 10/2010 | Dodde et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,909,820 B2 | 3/2011 | Lipson et al. |
| 7,931,649 B2 | 4/2011 | Couture et al. |
| 7,976,544 B2 | 7/2011 | McClurken et al. |
| 8,034,049 B2 | 10/2011 | Odom et al. |
| 8,034,051 B2 | 10/2011 | Martin et al. |
| D649,249 S | 11/2011 | Guerra |
| D649,643 S | 11/2011 | Allen, IV et al. |
| 8,162,940 B2 | 4/2012 | Johnson et al. |
| 8,187,273 B2 | 5/2012 | Kerr et al. |
| D661,394 S | 6/2012 | Romero et al. |
| 8,197,472 B2 | 6/2012 | Lau et al. |
| 8,226,649 B2 | 7/2012 | Falkenstein et al. |
| 8,277,446 B2 | 10/2012 | Heard |
| 8,292,879 B2 | 10/2012 | Manwaring et al. |
| D670,808 S | 11/2012 | Moua et al. |
| 8,303,585 B2 | 11/2012 | Mollenauer |
| 8,372,066 B2 | 2/2013 | Manwaring et al. |
| 8,377,052 B2 | 2/2013 | Manwaring et al. |
| 8,394,094 B2 | 3/2013 | Edwards et al. |
| D680,220 S | 4/2013 | Rachlin |
| 8,425,503 B2 | 4/2013 | Manwaring et al. |
| 8,491,578 B2 | 7/2013 | Manwaring et al. |
| 8,491,626 B2 | 7/2013 | Roy et al. |
| 8,523,850 B2 | 9/2013 | Manwaring et al. |
| 8,523,852 B2 | 9/2013 | Manwaring et al. |
| 8,551,088 B2 | 10/2013 | Falkenstein et al. |
| 8,562,598 B2 | 10/2013 | Falkenstein et al. |
| 8,568,411 B2 | 10/2013 | Falkenstein et al. |
| 8,597,293 B2 | 12/2013 | Falkenstein et al. |
| 8,597,297 B2 | 12/2013 | Couture et al. |
| 8,617,151 B2 | 12/2013 | Denis et al. |
| 8,623,003 B2 | 1/2014 | Lau et al. |
| 8,636,730 B2 | 1/2014 | Keppel |
| 8,734,445 B2 | 5/2014 | Johnson et al. |
| 8,915,909 B2 | 12/2014 | Manwaring et al. |
| 8,932,279 B2 | 1/2015 | Stringham et al. |
| 8,951,248 B2 | 2/2015 | Messerly et al. |
| 9,005,199 B2 | 4/2015 | Beckman et al. |
| 9,039,694 B2 | 5/2015 | Ross et al. |
| 9,050,100 B2 | 6/2015 | Yates et al. |
| 9,084,606 B2 | 7/2015 | Greep |
| 9,131,977 B2 | 9/2015 | Manwaring et al. |
| 9,149,321 B2 | 10/2015 | Stringham et al. |
| 9,192,427 B2 | 11/2015 | Johnson et al. |
| 9,265,553 B2 | 2/2016 | Manwaring et al. |
| 9,265,554 B2 | 2/2016 | Manwaring et al. |
| 9,265,555 B2 | 2/2016 | Manwaring et al. |

(56) References Cited

U.S. PATENT DOCUMENTS

| | | |
|---|---|---|
| 9,265,556 B2 | 2/2016 | Manwaring et al. |
| 9,320,560 B2 | 4/2016 | Manwaring et al. |
| 9,387,037 B2 | 7/2016 | Yang |
| 9,402,679 B2 | 8/2016 | Ginnebaugh et al. |
| 9,579,146 B2 | 2/2017 | Johnson et al. |
| 9,915,831 B2 | 3/2018 | Hue |
| 9,918,774 B2 | 3/2018 | Batchelor et al. |
| 9,931,157 B2 | 4/2018 | Strobl et al. |
| 9,955,858 B2 | 5/2018 | Pamnani et al. |
| 10,085,794 B2 | 10/2018 | Kerr et al. |
| 10,204,773 B2 | 2/2019 | Sugiyama et al. |
| 10,213,247 B2 | 2/2019 | Manwaring et al. |
| 10,610,289 B2 | 4/2020 | Jensen |
| 2007/0265616 A1 | 11/2007 | Couture et al. |
| 2008/0009860 A1 | 1/2008 | Odom |
| 2008/0172052 A1* | 7/2008 | Eder ............... A61B 18/1442 606/50 |
| 2009/0204114 A1 | 8/2009 | Odom |
| 2010/0076427 A1* | 3/2010 | Heard ............. A61B 18/1442 606/45 |
| 2010/0217264 A1 | 8/2010 | Odom et al. |
| 2012/0116391 A1 | 5/2012 | Houser |
| 2012/0248167 A1 | 10/2012 | Flanagan et al. |
| 2012/0283731 A1 | 11/2012 | Unger et al. |
| 2013/0041367 A1 | 2/2013 | Wham et al. |
| 2013/0253489 A1 | 9/2013 | Nau, Jr. et al. |
| 2014/0135804 A1 | 5/2014 | Weisenburgh, II et al. |
| 2014/0142574 A1 | 5/2014 | Heard |
| 2015/0088122 A1* | 3/2015 | Jensen ............. A61B 18/1445 606/37 |
| 2015/0141981 A1* | 5/2015 | Price ............... A61B 18/1445 606/38 |
| 2016/0143687 A1* | 5/2016 | Hart ............... A61B 18/1442 29/525 |
| 2017/0156788 A1 | 6/2017 | Johnson et al. |
| 2017/0196648 A1 | 7/2017 | Ward et al. |
| 2017/0224407 A1* | 8/2017 | Takami ............ A61B 18/1442 |
| 2017/0296212 A1* | 10/2017 | Ding ................. A61B 17/295 |
| 2018/0206905 A1* | 7/2018 | Batchelor ........... A61B 18/14 |
| 2018/0303322 A1 | 10/2018 | Pamnani et al. |
| 2019/0000538 A1 | 1/2019 | Widenhouse et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1080694 A1 | 3/2001 |
| EP | 1281878 A1 | 2/2003 |
| EP | 1159926 A2 | 3/2003 |
| JP | 61501068 A | 5/1986 |
| JP | H1024051 | 1/1989 |
| JP | 55106 | 1/1993 |
| JP | H0540112 A | 2/1993 |
| JP | 6121797 A | 5/1994 |
| JP | 6285078 A | 10/1994 |
| JP | 6511401 | 12/1994 |
| JP | H06343644 A | 12/1994 |
| JP | H07265328 A | 10/1995 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |
| JP | 9122138 A | 5/1997 |
| JP | 0010000195 A | 1/1998 |
| JP | H1147149 A | 2/1999 |
| JP | H1147150 A | 2/1999 |
| JP | 2011192238 A | 7/1999 |
| JP | H11244298 A | 9/1999 |
| JP | H11294773 A | 10/1999 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029355 | 2/2001 |
| JP | 2001128990 A | 5/2001 |
| JP | 2001190564 A | 7/2001 |
| JP | 2002136525 A | 5/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011070124 A | 4/2011 |
| JP | 2011125195 A | 6/2011 |
| JP | 2011169381 A | 9/2011 |
| JP | H0630945 B2 | 11/2016 |
| SU | 401367 A1 | 10/1973 |
| WO | 0024330 A1 | 5/2000 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

\* cited by examiner

SYSTEMS AND METHODS FOR SEALING AND DISSECTING TISSUE USING AN ELECTROSURGICAL FORCEPS INCLUDING A THERMAL CUTTING ELEMENT

FIELD

The disclosure relates to electrosurgical systems and, more particularly, to systems and methods for sealing and dissecting tissue with an electrosurgical instrument including a thermal cutting element.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the disclosure is a method for treating tissue. The method includes determining whether tissue is present between first and second jaw members and, in a case where it is determined that tissue is present between the first and second jaw members, determining whether activation has been initiated. In a case where it is determined that activation has been initiated, the method includes supplying electrosurgical energy to the first and second jaw members to seal the tissue present between the jaw members and determining if the sealing is complete. In a case where it is determined that sealing is complete, the method further includes: stopping the supply of electrosurgical energy: activating a thermal cutting element to supply thermal energy to cut the sealed tissue; determining if thermal cutting is complete; and, in a case where it is determined that the thermal cutting is complete, stopping the supply of thermal energy.

In an aspect of the present disclosure, activating the thermal cutting element may further include determining if a first thermal mode and/or a second thermal mode is activated. In a case where the first thermal mode is activated, the method includes activating the thermal cutting element in a high temperature mode; and, in a case where the second thermal mode is activated, activating the thermal cutting includes activating the thermal cutting element in a low temperature mode. The thermal cutting element is heated to a lower temperature in the low temperature mode as compared to the high temperature mode.

In another aspect of the present disclosure, the method may further include, in a case where it is determined that tissue is not present between the jaw members: determining whether activation has been initiated; and, in a case where it is determined that activation has been initiated, activating the thermal cutting element to supply thermal energy to tissue to cut the tissue. The method may then include determining if the thermal cutting is complete based on one of power consumption, temperature exceeding a predetermined threshold, and/or time exceeding a predetermined threshold. If it is determined that the thermal cutting is complete, the supply of thermal energy is stopped.

In another aspect of the present disclosure, the method may further include, in a case where it is determined that tissue is not present between the jaw members: determining whether activation has been initiated; and, in a case where it is determined that activation has been initiated, activating the thermal cutting element in a different mode to supply thermal energy to tissue to cut the tissue. The different mode is different from a mode of activation of the thermal cutting element to supply thermal energy to cut the sealed tissue. The method may further include determining if the thermal cutting is complete based on one of power consumption, temperature exceeding a predetermined threshold, and/or time exceeding a predetermined threshold. In a case where it is determined that the thermal cutting is complete, the supply of thermal energy is stopped.

In still another aspect of the present disclosure, the method further includes, in a case where it is determined that tissue is present between the first and second jaw members, displaying on a display an indication that tissue is present.

In yet another aspect of the present disclosure, the method may further include, in a case where it is determined that tissue is not present between the first and second jaw members, displaying on a display an indication that tissue is not present.

In still yet another aspect of the present disclosure, the method may further include, in a case where it is determined that the sealing is not complete, emitting a fault tone.

In an aspect of the present disclosure, the method may further include displaying on a display a fault condition.

In another aspect of the present disclosure, the method may further include, in a case where the sealing is complete, emitting a success tone.

In an aspect of the present disclosure, determining if the thermal cutting is complete may be based on power consumption, temperature exceeding a predetermined threshold, and/or time exceeding a predetermined threshold.

In still yet another aspect of the present disclosure, determining tissue presence between the first and second jaw members may be based on sensing impedance between the first and second jaw members.

Provided in accordance with aspects of the disclosure is a system for treating tissue. The system includes: a surgical instrument, a processor, and a memory coupled to the processor. The surgical instrument includes first and second jaw members configured to treat tissue. The first or second jaw member includes a thermal cutting element and each of the first and second jaw members includes a sealing surface. The memory has instructions stored thereon which, when executed by the processor, cause the system to: determine whether tissue is present between first and second jaw members based on sensing impedance between the sealing surfaces of the first and second jaw members. In a case where it is determined that tissue is present between the first and second jaw members, the system is further caused to determine whether activation has been initiated. In a case where it is determined that activation has been initiated, the system is further caused to supply electrosurgical energy to the first and second jaw members to seal the present tissue and determine if the sealing is complete. In a case where it is determined that the sealing is complete, the system is further caused to: stop the supply of electrosurgical energy: activate a thermal cutting element to supply thermal energy to cut the sealed present tissue: determine if thermal cutting is complete based on power consumption, temperature exceeding a predetermined threshold, and/or time exceeding a predetermined threshold; and, in a case where it is determined that the thermal cutting is complete, stop the supply of thermal energy.

In an aspect of the present disclosure, activating the thermal cutting element may further include: determining if a first thermal mode or a second thermal mode is activated: in a case where the first thermal mode is activated, activating the thermal cutting element in a high temperature mode; and in a case where the second thermal mode is activated, activating the thermal cutting element in a low temperature mode, wherein the thermal cutting element is heated to a lower temperature in the low temperature mode as compared to the high temperature mode.

In another aspect of the present disclosure, the instructions, when executed by the processor, may further cause the system to: in a case where it is determined that tissue is not present between the jaw members: determining whether activation has been initiated: in a case where it is determined that activation has been initiated, activating the thermal cutting element to supply thermal energy to tissue to cut the tissue; and determining if thermal cutting is complete based on power consumption, temperature exceeding a predetermined threshold, and/or time exceeding a predetermined threshold; and if it is determined that the thermal cutting is complete, stopping the supply of thermal energy.

In another aspect of the present disclosure, the instructions, when executed by the processor, may further cause the system to: in a case where it is determined that tissue is not present between the jaw members: determining whether activation has been initiated: in a case where it is determined that activation has been initiated, activating the thermal cutting element in a different mode to supply thermal energy to tissue to cut the tissue, wherein the different mode is different from a mode of activation of the thermal cutting element to supply thermal energy to cut the sealed tissue; and determining if the different thermal cutting is complete based on power consumption, temperature exceeding a predetermined threshold, and/or time exceeding a predetermined threshold; and in a case where it is determined that the thermal cutting is complete, stopping the supply of thermal energy.

In still another aspect of the present disclosure, the instructions, when executed by the processor, may further cause the system to, in a case where it is determined that tissue is present between the first and second jaw members, displaying, on a display, an indication that tissue is present.

In yet another aspect of the present disclosure, the instructions, when executed by the processor, may further cause the system, in a case where it is determined that tissue is not present between the first and second jaw members, to display, on a display, an indication that tissue is not present.

In still yet another aspect of the present disclosure, the instructions, when executed by the processor, may further cause the system, in a case where it is determined that the sealing is not complete, to emit a fault tone.

In an aspect of the present disclosure, the instructions, when executed by the processor, may further cause the system to display, on a display, a fault condition.

Provided in accordance with aspects of the disclosure is a non-transitory storage medium that stores a program causing a computer to execute a method for controlling delivery of tissue dissection with a thermal cutter. The method includes determining whether tissue is present between first and second jaw members and, in a case where it is determined that tissue is present between the first and second jaw members, determining whether activation has been initiated. In a case where it is determined that activation has been initiated, the method further includes supplying electrosurgical energy to the first and second jaw members to seal the tissue present between the jaw members and determining if the sealing is complete. In a case where it is determined that sealing is complete, the method further includes: stopping the supply of electrosurgical energy: activating a thermal cutting element to supply thermal energy to cut the sealed tissue: determining if thermal cutting is complete; and, in a case where it is determined that the thermal cutting is complete, stopping the supply of thermal energy.

BRIEF DESCRIPTION OF DRAWINGS

The above and other aspects and features of the disclosure will become more apparent in view of the following detailed description when taken in conjunction with the accompanying drawings wherein like reference numerals identify similar or identical elements.

DETAILED DESCRIPTION

The disclosure relates to electrosurgical systems and methods and, more particularly, to electrosurgical forceps including thermal cutting elements to facilitate tissue treatment, e.g., sealing and/or cutting tissue. Although portions of the disclosure discuss particular types of energy-based surgical systems, the disclosure is equally applicable to other types of energy-based surgical systems not expressly described herein.

Figure 1:
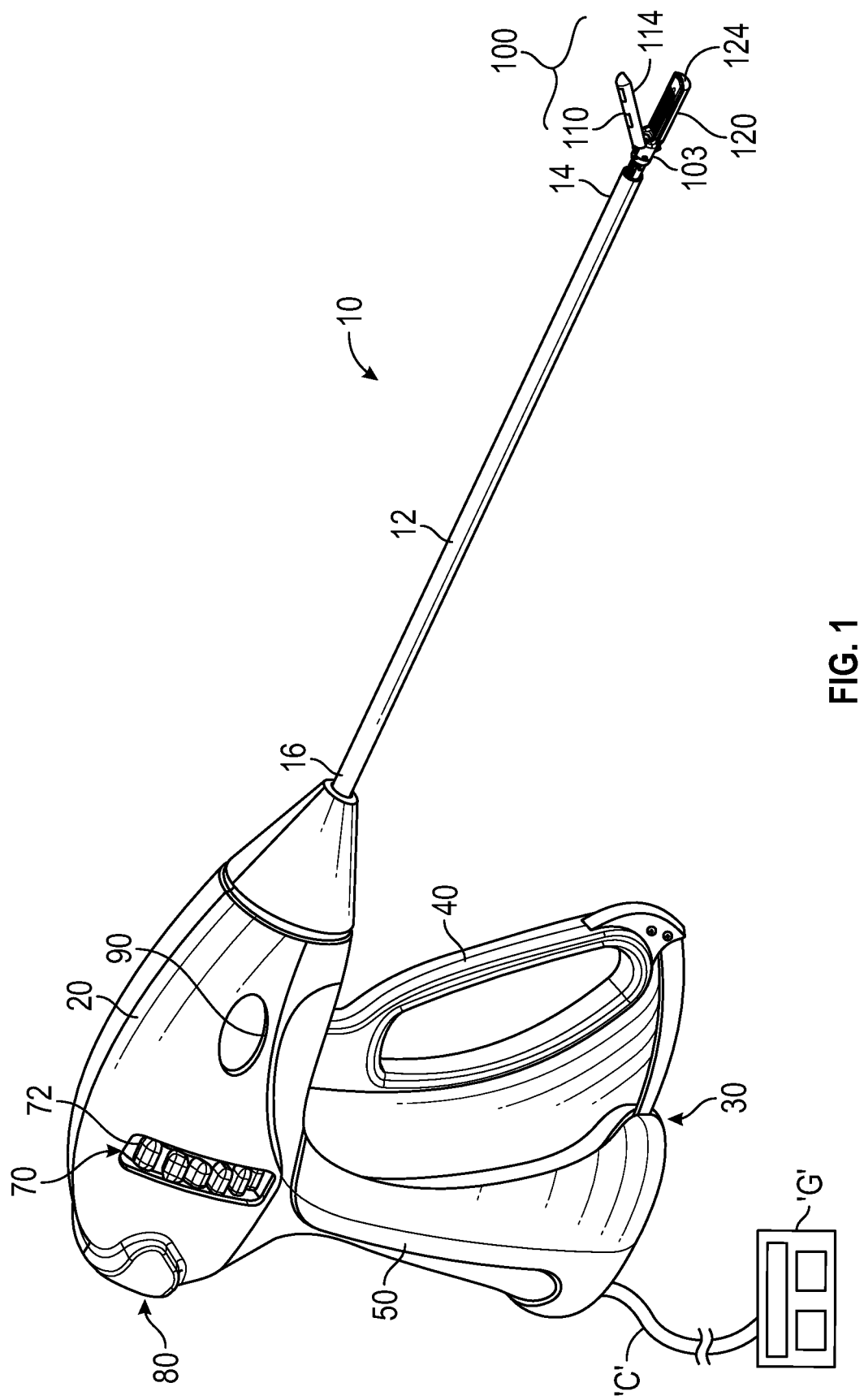
FIG. 1 is a perspective view of a shaft-based electrosurgical forceps provided in accordance with the disclosure shown connected to an electrosurgical generator.

Referring to FIG. 1, a shaft-based electrosurgical forceps provided in accordance with the disclosure is shown generally identified by reference numeral 10. Aspects and features of forceps 10 not germane to the understanding of the disclosure are omitted to avoid obscuring the aspects and features of the disclosure in unnecessary detail.

Forceps 10 includes a housing 20, a handle assembly 30, a rotating assembly 70, a first activation switch 80, a second activation switch 90, and an end effector assembly 100.

Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "G." Cable "C" includes a wire (or wires) (not shown) extending therethrough that has sufficient length to extend through shaft 12 in order to connect to one or both tissue-treating surfaces 114, 124 of jaw members 110, 120, respectively, of end effector assembly 100 (see FIG. 4) to provide energy thereto. First activation switch 80 is coupled to tissue-treating surfaces 114, 124 (FIG. 4) and the electrosurgical generator "G" for enabling the selective activation of the supply of energy to jaw members 110, 120 for treating, e.g., cauterizing, coagulating/desiccating, and/or sealing, tissue. Second activation switch 90 is coupled to thermal cutting element 130 of jaw member 120 (FIG. 4) and the electrosurgical generator "G" for enabling the selective activation of the supply of energy to thermal cutting element 130 of jaw member 120 (FIG. 4) for thermally cutting tissue. In various embodiments, a multimode and/or a single activation switch may be used.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position and an approximated position to grasp tissue between tissue-treating surfaces 114, 124 of jaw members 110, 120. As shown in FIG. 1, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120. Rotating assembly 70 includes a rotation wheel 72 that is selectively rotatable in either direction to correspondingly rotate end effector assembly 100 relative to housing 20.

Figure 2:
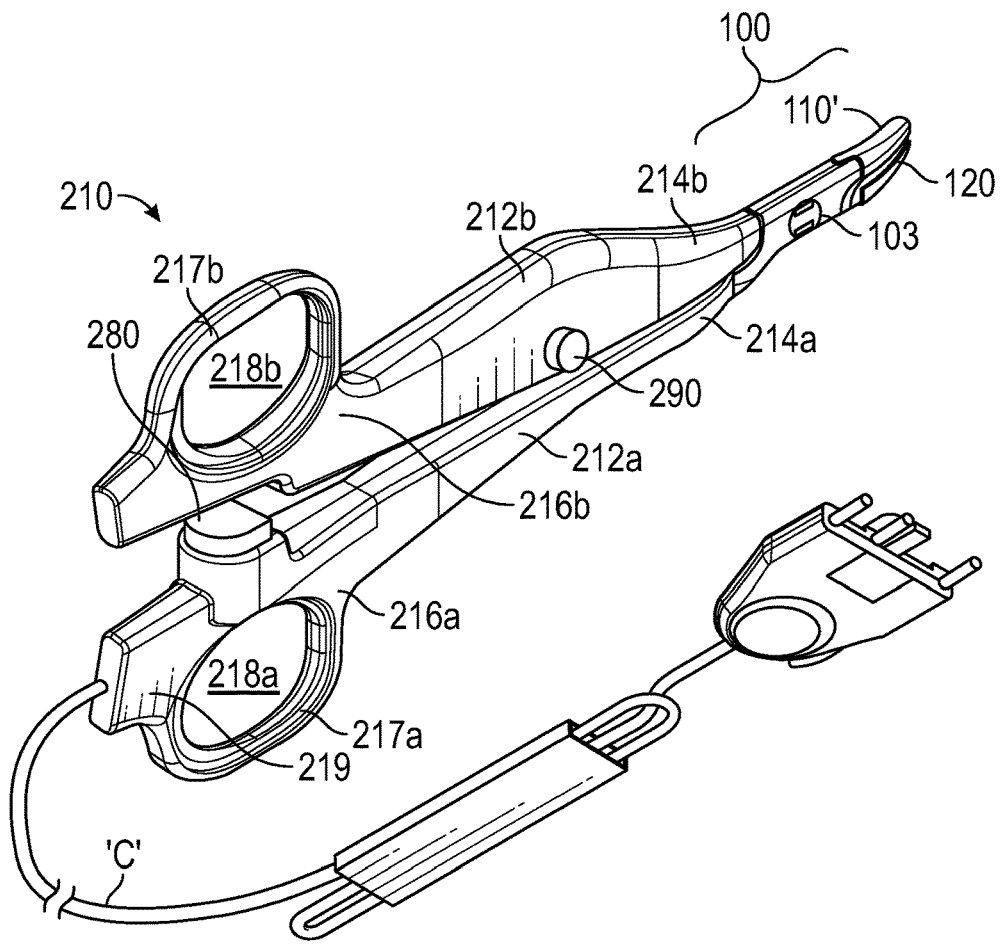
FIG. 2 is a perspective view of a hemostat-style electrosurgical forceps provided in accordance with the present disclosure.

Referring to FIG. 2, a hemostat-style electrosurgical forceps provided in accordance with the disclosure is shown generally identified by reference numeral 210. Aspects and features of forceps 210 not germane to the understanding of the disclosure are omitted to avoid obscuring the aspects and features of the disclosure in unnecessary detail.

Figure 4:
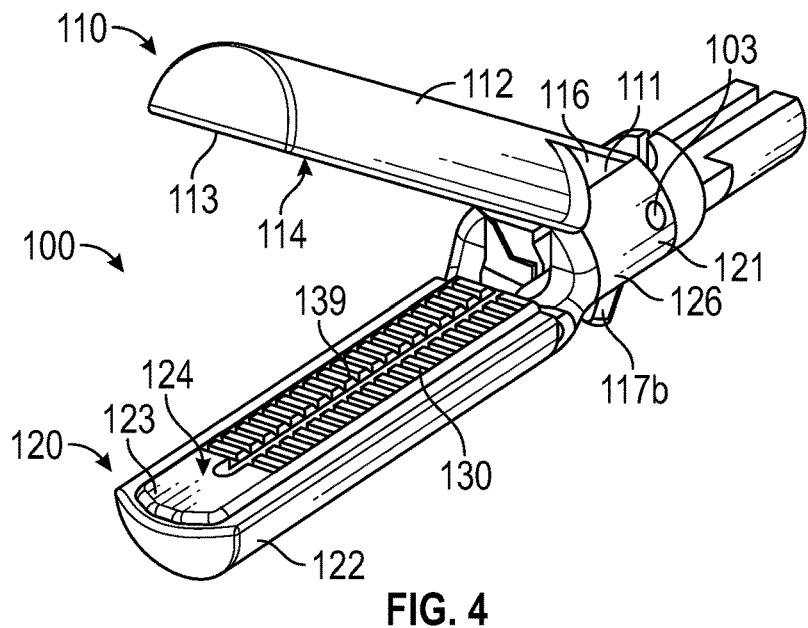
FIG. 4 is a perspective view of a distal end portion of the forceps of FIG. 1, wherein first and second jaw members of an end effector assembly of the forceps are disposed in a spaced-apart position.

Forceps 210 includes two elongated shaft members 212a, 212b, each having a proximal end portion 216a, 216b, and a distal end portion 214a, 214b, respectively. Forceps 210 is configured for use with an end effector assembly 100' similar to end effector assembly 100 (FIG. 4). More specifically, end effector assembly 100' includes first and second jaw members 110', 120' attached to respective distal end portions 214a, 214b of shaft members 212a, 212b. Jaw members 110', 120' are pivotably connected about a pivot 103'. Each shaft member 212a, 212b includes a handle 217a, 217b disposed at the proximal end portion 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212a, 212b of forceps 210, e.g., shaft member 212a, includes a proximal shaft connector 219 configured to connect forceps 210 to a source of energy, e.g., electrosurgical generator "G" (FIG. 1). Proximal shaft connector 219 secures a cable "C" to forceps 210 such that the user may selectively supply energy to jaw members 110', 120' for treating tissue. More specifically, a first activation switch 280 is provided for supplying energy to jaw members 110', 120' to treat tissue upon sufficient approximation of shaft members 212a, 212b, e.g., upon activation of first activation switch 280 via shaft member 212b. A second activation switch 290 disposed on either or both of shaft members 212a, 212b is coupled to the thermal cutting element (not shown, similar to thermal cutting element 130 of jaw member 120 (FIG. 4)) of one of the jaw members 110', 120' of end effector assembly 100' and to the electrosurgical generator "G" for enabling the selective activation of the supply of energy to the thermal cutting element for thermally cutting tissue.

Jaw members 110', 120' define a curved configuration wherein each jaw member is similarly curved laterally off of a longitudinal axis of end effector assembly 100'. However, other suitable curved configurations including curvature towards one of the jaw members 110, 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
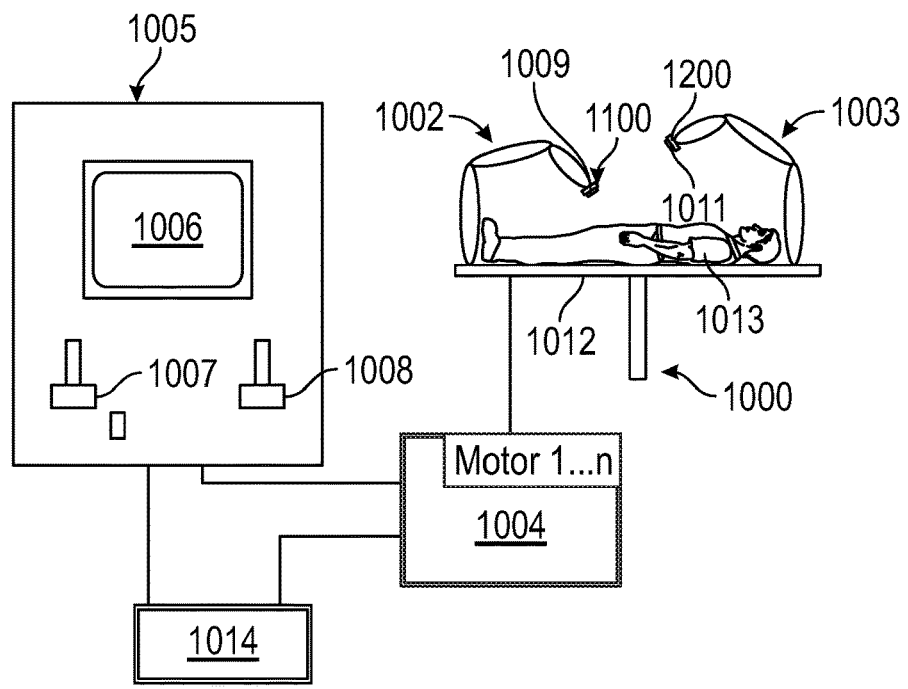
FIG. 3 is a schematic illustration of a robotic surgical system provided in accordance with the present disclosure.

Referring to FIG. 3, a robotic surgical system provided in accordance with the disclosure is shown generally identified by reference numeral 1000. Aspects and features of robotic surgical system 1000 not germane to the understanding of the disclosure are omitted to avoid obscuring the aspects and features of the disclosure in unnecessary detail.

Robotic surgical system 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

The control device 1004 includes a processor connected to a computer-readable storage medium or a memory which may be a volatile type memory, such as RAM, or a non-volatile type memory, such as flash media, disk media, or other types of memory. In various embodiments, the processor may be another type of processor such as, without limitation, a digital signal processor, a microprocessor, an ASIC, a graphics processing unit (GPU), field-programmable gate array (FPGA), or a central processing unit (CPU).

In various embodiments, the memory can be random access memory, read-only memory, magnetic disk memory, solid-state memory, optical disc memory, and/or another type of memory. In various embodiments, the memory can be separate from the control unit and can communicate with the processor through communication buses of a circuit board and/or through communication cables such as serial ATA cables or other types of cables. The memory includes computer-readable instructions that are executable by the processor to operate the control device 1004. In various embodiments, the control device 1004 may include a network interface to communicate with other computers or a server.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to end effector assembly 100 (FIG. 4), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 5A:
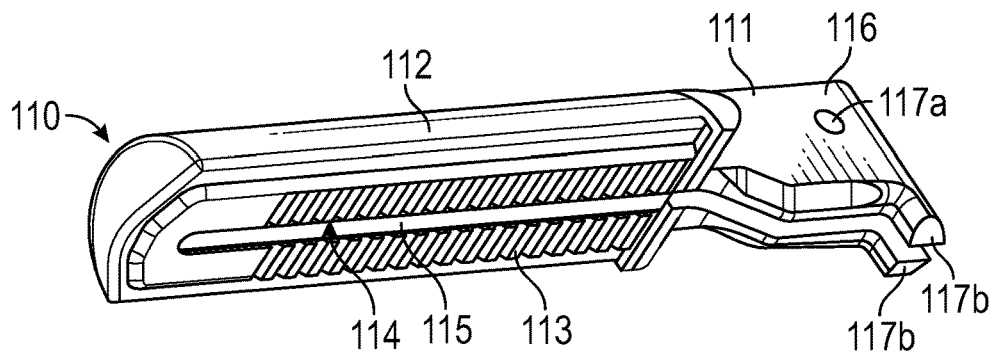
FIG. 5A is a bottom, perspective view of the first jaw member of the end effector assembly of FIG. 4.
Figure 5B:
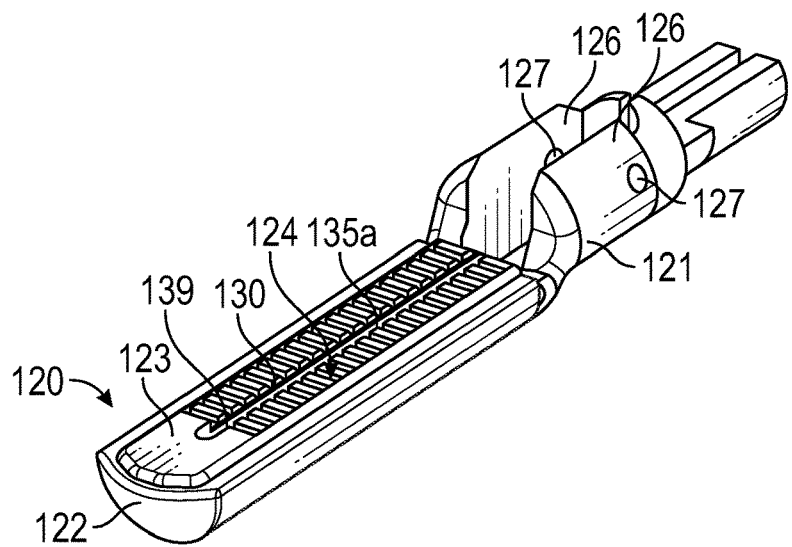
FIG. 5B is a top, perspective view of the second jaw member of the end effector assembly of FIG. 4.

Turning to FIGS. 4-5B, end effector assembly 100, as noted above, includes first and second jaw members 110, 120. Each jaw member 110, 120 may include a structural frame 111, 121, a jaw housing 112, 122, and one or more tissue-treating plates 113, 123 defining the respective tissue-treating surface 114, 124 thereof. Alternatively, only one of the jaw members, e.g., jaw member 120, may include a structural frame 121, jaw housing 122, and tissue-treating plate 123 defining the tissue-treating surface 124. In such embodiments, the other jaw member, e.g., jaw member 110, may be formed as a single unitary body, e.g., a piece of conductive material acting as the structural frame 111 and jaw housing 112 and defining the tissue-treating surface 114. An outer surface of the jaw housing 112, in such embodiments, may be at least partially coated with an insulative material or may remain exposed.

Referring in particular to FIGS. 4 and 5A, jaw member 110, as noted above, may be configured similarly as jaw member 120, may be formed as a single unitary body, or may be formed in any other suitable manner so as to define a tissue-treating surface 114 opposing tissue-treating surface 124 of jaw member 120 and a structural frame 111. Structural frame 111 includes a proximal flange portion 116 about which jaw member 110 is pivotably coupled to jaw member 120. In shaft-based or robotic embodiments, proximal flange portion 116 may further include an aperture 117a for receipt of pivot 103 and at least one protrusion 117b extending therefrom that is configured for receipt within an aperture defined within a drive sleeve of the drive assembly (not shown) such that translation of the drive sleeve, e.g., in response to actuation of movable handle 40 (FIG. 1) or a robotic drive, pivots jaw member 110 about pivot 103 and relative to jaw member 120 between the spaced-apart position and the approximated position. However, other suitable drive arrangements are also contemplated, e.g., using cam pins and cam slots, a screw-drive mechanism, etc.

Regardless of the particular configuration of jaw member 110, jaw member 110 further includes a longitudinally-extending insulative member 115 extending along at least a portion of the length of tissue-treating surface 114. In embodiments, the insulative member 115 may be omitted and the tissue-treating plates 113, 123 may extend all the way across the jaw member 110, 120. Insulative member 115 may be transversely centered on tissue-treating surface 114 or may be offset relative thereto. Further, insulative member 115 may be disposed. e.g., deposited, coated, etc., on tissue-treating surface 114, may be positioned within a channel or recess defined within tissue-treating surface 114, or may define any other suitable configuration. Additionally, insulative member 115 may be substantially (within manufacturing, material, and/or use tolerances) coplanar with tissue-treating surface 114, may protrude from tissue-treating surface 114, may be recessed relative to tissue-treating surface 114, or may include different portions that are coplanar, protruding, and/or recessed relative to tissue-treating surface 114. Insulative member 115 may be formed from, for example, ceramic, parylene, nylon. PTFE, or other suitable material(s) (including combinations of insulative and non-insulative materials).

With reference to FIGS. 4, and 5B, as noted above, jaw member 120 includes a structural frame 121, a jaw housing 122, and a tissue-treating plate 123 defining the tissue-treating surface 124 thereof. Jaw member 120 further includes a thermal cutting element 130 mounted thereon. Structural frame 121 defines a proximal flange portion 126 and a distal body portion (not shown) extending distally from proximal flange portion 126. Proximal flange portion 126 is bifurcated to define a pair of flanges having aligned apertures 127 configured for receipt of pivot 103 therethrough to pivotably couple jaw members 110, 120 with one another. Thermal cutting element 130, defines an upper, tissue-treating surface 135a which may be flat, angled, pointed, curved, or include any suitable configuration. In embodiments where end effector assembly 100, or a portion thereof, is curved, structural frame 121 and thermal cutting element 130, or corresponding portions thereof, may similarly be curved, e.g., wherein structural frame 121 and thermal cutting element 130 (or corresponding portions thereof) are relatively configured with reference to an arc (or arcs) of curvature rather than a longitudinal axis. Thus, the terms longitudinal, transverse, and the like as utilized herein are not limited to linear configurations, e.g., along linear axes, but apply equally to curved configurations, e.g., along arcs of curvature. In various embodiments, thermal cutting element 130 may extend all the way to or beyond the distal end of the jaw member 110, 120.

Jaw housing 122 may be formed from an electrically insulative material and includes one or more portions (separate or unitary) formed in any suitable manner such as, for example, via overmolding. More specifically, in embodiments, a first overmold may capture structural frame 121 and cutting element 130 while a second overmold captures tissue-treating plate 123, the first overmold, structural frame 121, and cutting element 130 to maintain plate 123 isolated from frame 121 and element 130. Alternatively, only the second overmold may be provided to capture tissue-treating plate 123, structural frame 121, and cutting element 130 (while still maintaining the isolation therebetween). As another alternative, an insulative insert may form a portion of jaw housing 122 together with or in place of either or both overmolds. The insulative material, in any of the above configurations, may fill only a portion of the interior of jaw member 120 such that the interior is at least partially hollow, or may fill the substantial entirety of the interior of jaw member 120. Other suitable configurations are also contemplated.

Regardless of the particular configuration of jaw housing 122, the assembled jaw member 120 includes tissue-treating plate 123 defining tissue-treating surface 124 and tissue-treating surface 135a of thermal cutting element 130 substantially (within manufacturing, material, and/or use tolerances) coplanar with tissue-treating surface 124, protruding from tissue-treating surface 124, recessed relative to tissue-treating surface 124, or provided in any other suitable manner. In aspects, the thermal cutting element 130 may define a variable height, e.g., tapering proximally-to-distally, such that tissue-treating surface 135a is angled relative to tissue-treating surface 124, e.g., to cut tissue heel first. Tissue-treating plate 123, more specifically, may define a channel 139 through which thermal cutting element 130 at least partially extends such that tissue-treating surface 135a thereof is exposed. The remainder of channel 139 may be filled with an insulative material, e.g., a portion jaw housing 122 or other insulator, to isolate thermal cutting element 130 from tissue-treating plate 123. In the closed position of jaw members 110, 120, tissue-treating surface 135a of cutting element 130 is configured to oppose insulative member 115 to isolate thermal cutting element 130 from tissue-treating plate 113.

Generally referring to FIGS. 1-5B, tissue-treating plates 113, 123 are formed from an electrically conductive material, e.g., for conducting electrical energy therebetween for treating tissue, although tissue-treating plates 113, 123 may alternatively be configured to conduct any suitable energy, e.g., thermal, microwave, light, ultrasonic, etc., through tissue grasped therebetween for energy-based tissue treatment. As mentioned above, tissue-treating plates 113, 123 are coupled to activation switch 80 and electrosurgical generator "G" (FIG. 1) such that energy may be selectively supplied to tissue-treating plates 113, 123 and conducted therebetween and through tissue disposed between jaw members 110, 120 to treat tissue, e.g., seal tissue on either side and extending across of thermal cutting element 130.

Thermal cutting element 130, on the other hand, is configured to connect to electrosurgical generator "G" (FIG. 1) and second activation switch 90 to enable selective activation of the supply of energy to thermal cutting element 130 for heating thermal cutting element 130 to thermally cut tissue disposed between jaw members 110, 120, e.g., to cut the sealed tissue into first and second sealed tissue portions. Other configurations including multi-mode switches, other separate switches, a single switch for automatic activation, etc. may alternatively be provided.

Thermal cutting element 130 may be any suitable thermal cutting element such as, for example, an aluminum substrate that is Plasma Electrolytic Oxidation (PEO)-treated at least along a portion of tissue-treating surface 135a. The thermal cutting element 130 may include a resistive element such that when an AC voltage is applied, resistive element is heated for thermally cutting tissue. As another example, thermal cutting element 130 may be configured as a ferromagnetic (FM) element including a core, e.g., copper, and a ferromagnetic material coated on the core such that when an AC or DC voltage is applied, the FM element is heated up to the Curie point for thermally cutting tissue. Other suitable cutting element configurations are also contemplated. The above-detailed configuration of structural frame 121 of jaw member 120 and thermal cutting element 130, e.g., wherein there is minimal contact or approximation therebetween (only at the proximal and distal ends of thermal cutting element 130) and where free space or insulator is otherwise disposed therebetween, reduces thermal heating of structural frame 121 of jaw member 120 when thermal cutting element 130 is heated (by reducing the conductive pathways for heat to travel to structural frame 121), thus helping to reduce the overall temperature of jaw member 120 and facilitate cooling after use.

Figure 6:
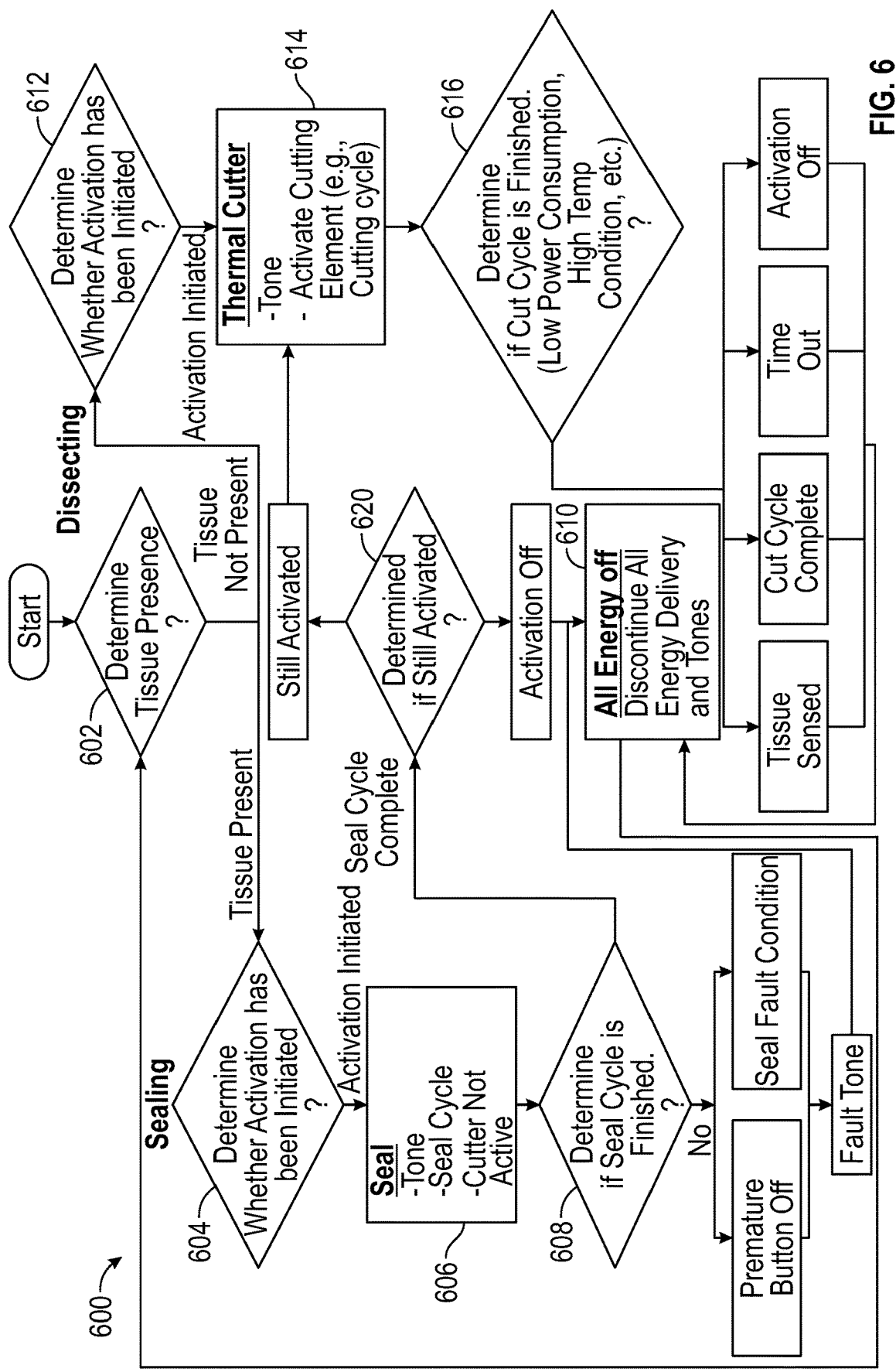
FIG. 6 is a flowchart of a method for tissue sealing and dissection in accordance with aspects of the disclosure.

Referring now to FIG. 6, there is shown a flow diagram of a computer implemented method 600 for tissue sealing and dissection using an electrosurgical end effector assembly including first and second jaw members and a thermal cutting element, e.g., such as the end effector assemblies detailed above. Persons skilled in the art will appreciate that one or more operations of the method 600 may be performed in a different order, repeated, and/or omitted without departing from the scope of the disclosure. In various embodiments, some or all of the operations in the illustrated method 600 can operate using an electrosurgical forceps, e.g., instrument 10 or 210 (see FIGS. 1 and 2) and the generator "G" (see FIG. 1), or with robotic surgical system 1000. Other variations are contemplated to be within the scope of the disclosure. The operations of FIG. 6 will be described with respect to a control device, e.g., control device 1004 of robotic surgical system 1000 (FIG. 3), a control device incorporated into instrument 10 or 210 (see FIGS. 1 and 2), a control device incorporated into generator "G" (see FIG. 1), or any other suitable control device or location thereof including a remotely-disposed control device. It will be understood that the illustrated operations are applicable to other systems and components thereof as well.

Initially at step 602, the control device determines whether tissue is present between the first and second jaw members. The presence of tissue includes where tissue is between and contacting the sealing surfaces of the first and second jaw members. In embodiments, the control device determines tissue presence between the first and second jaw members based on sensing impedance between the first and second jaw members, e.g., if an impedance is determined, it is determined that tissue is present between the first and second jaw members and if an impedance cannot be determined, it is determined that tissue is not present between the first and second jaw members. In embodiments, the control device determines tissue presence between the first and second jaw members based on a proximity sensor, vision system, and/or jaw aperture. For example, the jaw members may include an imaging device and a processor to detect the presence of tissue. In various embodiments, the control device may determine tissue presence after the activation button is engaged. In various embodiments, when the control device determines that tissue is or is not present between the first and second jaw members, an indication that tissue is or is not present is displayed on a display, e.g., display 1006 (FIG. 3), a display of generator "G" (FIG. 1), or other suitable display.

If the control device determines that tissue is present at step 602, the method proceeds to step 604 where the control device determines whether activation has been initiated. For example, the control device may determine that a first activation switch 80, 280 (FIGS. 1 and 2, respectively) is engaged.

Next, at step 606, when the control device 1004 determines that activation has been initiated, electrosurgical energy is supplied to the first and second jaw members in accordance with a seal cycle algorithm or other suitable algorithm to seal the tissue present, e.g., grasped, between the jaw members. In various embodiments, the control device 1004 may emit, for example a tone, to signal that electrosurgical energy is being supplied to the first and second jaw members.

Next, at step 608, the control device determines if the seal cycle is complete, e.g., if the tissue has been sealed. In various embodiments, if the seal cycle is complete, the control device emits a success tone. In various embodiments, if the control device determines that the seal cycle is not complete and, thus, that tissue has not been sealed, the control device emits a fault tone. In various embodiments, the control device displays on the display a fault condition. The seal cycle may not complete and, thus, tissue may not be sealed, if, for example, the activation button is prematurely disengaged, due to a fault condition, and/or for other reasons. If the control device determines that the seal cycle is not complete, the method proceeds to step 610 and the supply of electrosurgical energy is ceased.

If it is determined that the seal cycle is complete, the method proceeds to step 620 where the control device determines if the activation switch is still engaged. If the control device determines that the activation switch is still engaged after the seal cycle is complete, the method proceeds to step 614 where the control device emits a tone signaling that dissection will begin. Continuing with step 614, the control device activates a thermal cutting element in accordance with a thermal cutting cycle (or other suitable algorithm) to supply thermal energy to the thermal cutting element, e.g., thermal cutting element 130 (FIGS. 4 and 5B) for thermally cutting the previously sealed tissue grasped between the jaw members. At step 616, the control device determines if the thermal cutting cut cycle is complete. If the thermal cutting cut cycle is determined to be complete, the control device stops the supply of thermal energy at step 610. In various embodiments, the control device determines if the thermal cutting cut cycle is complete based on power consumption, temperature exceeding a predetermined threshold, and/or time exceeding a predetermined threshold. In embodiments, a slow tone may indicate tissue sealing and a fast tone, faster than the slow tone, may indicate cutting tissue.

If the control device determines at step 608 that the first activation switch 80, 280 is not engaged and the seal cycle is complete, the method proceeds to step 610 where the control device stops the supply of electrosurgical energy.

If at step 602, the control device determines tissue is not present between the first and second jaw members, the control device determines whether activation has been initiated. For example, the control device may determine that the activation switch is engaged, at step 612. If the control device determines that activation has been initiated, the control device activates the thermal cutting element in accordance with the thermal cutting cycle to supply thermal energy to tissue to cut the tissue at step 614, as detailed above. The method them proceed to step 616 and continues as detailed above. In various embodiments, control device 1004 may determine that tissue is not grasped, and the thermal cutter may be activated (i.e., sealing is bypassed). This would allow the clinician to position the cutter against the tissue and transect through the tissue, for example, when minimal hemostasis is required.

Figure 7:
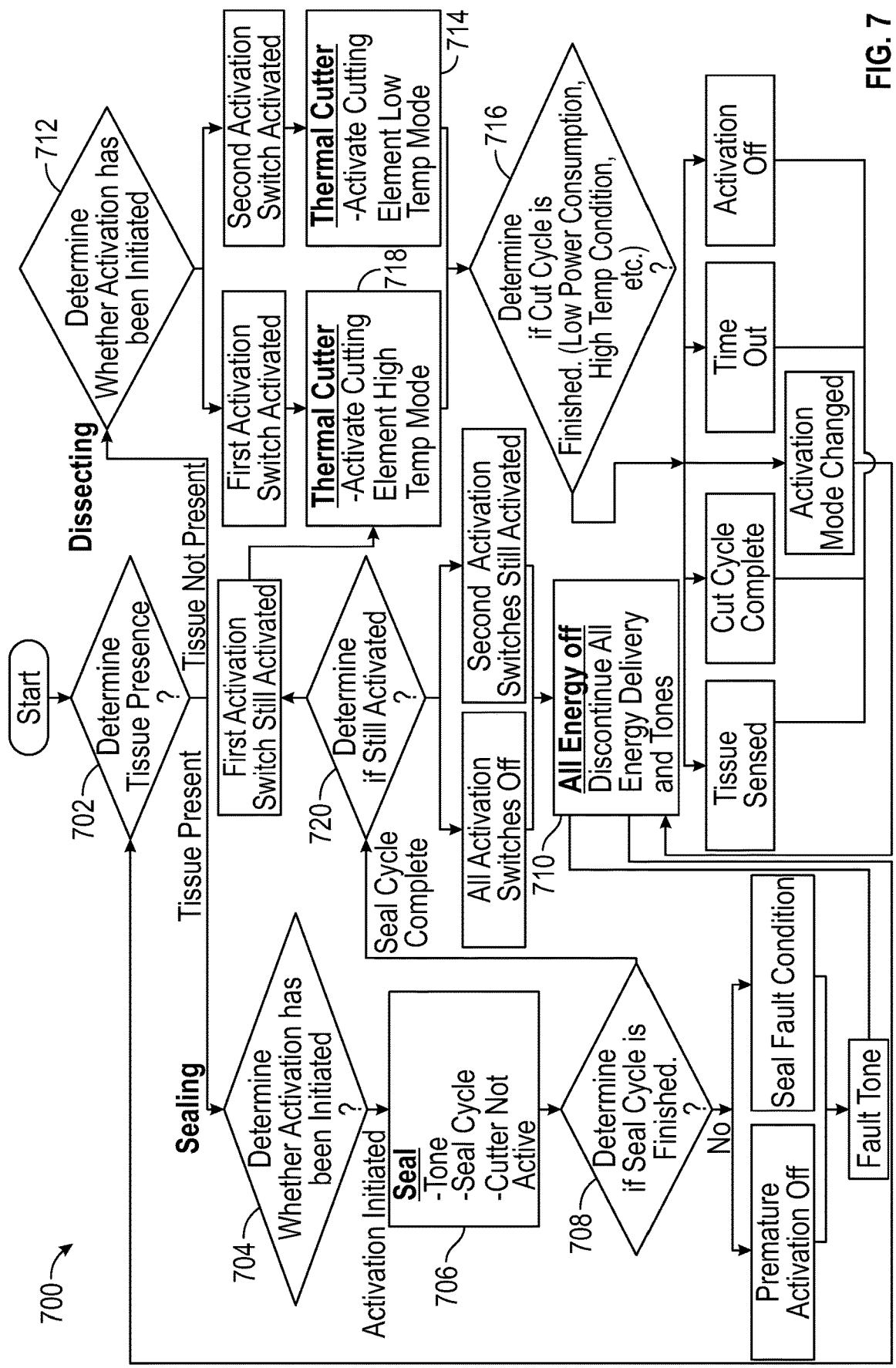
FIG. 7 is a flowchart of another method for tissue sealing and dissection in accordance with aspects of the disclosure.

Referring now to FIG. 7, there is shown a flow diagram of a computer implemented method 700 for tissue dissection using an electrosurgical end effector assembly including first and second jaw members and a thermal cutting element, e.g., such as the end effector assemblies detailed above. Persons skilled in the art will appreciate that one or more operations of the method 700 may be performed in a different order, repeated, and/or omitted without departing from the scope of the disclosure. In various embodiments, some or all of the operations in the illustrated method 700 can operate using electrosurgical forceps, e.g., instrument 10 or 210 (see FIGS. 1 and 2) and the generator "G" (see FIG. 1) or with robotic surgical system 1000. Other variations are contemplated to be within the scope of the disclosure. The operations of FIG. 7 will be described with respect to a control device, e.g., control device 1004 of robotic surgical system 1000 (FIG. 3), a control device incorporated into instrument 10 or 210 (see FIGS. 1 and 2), a control device incorporated into generator "G" (see FIG. 1), or any other suitable control device or location thereof including a remotely-disposed control device. It will be understood that the illustrated operations are applicable to other systems and components thereof as well.

Initially at step 702, the control device determines whether tissue is present between the first and second jaw members. In embodiments, the control device determines tissue presence between the first and second jaw members based on sensing impedance between the first and second jaw members, similarly as noted above. In various embodiments, when the control device determines that tissue is or is not present between the first and second jaw members, an indication that tissue is or is not present is displayed on a display. It is contemplated that the determination of the presence of tissue happens after activation has been initiated, e.g., that the order of steps 704 and 712 occur before step 702 (and similarly with respect to method 600 (FIG. 6)).

If the control device determines that tissue is present at step 702, the method proceeds to step 704, where the control device determines whether activation has been initiated. For example, the control device may determine whether a first activation switch, e.g., switch 80, 280 (FIGS. 1 and 2, respectively), and/or a second activation switch, e.g., switch 90, 290 (FIGS. 1 and 2, respectively), is engaged. It is contemplated that step 704 could be activated by either the first activation switch, e.g., switch 80, 280 (FIGS. 1 and 2, respectively), or the second activation switch, e.g., switch 90, 290 (FIGS. 1 and 2, respectively).

If it is determined that activation is initiated at step 706, e.g., that either or both switches are activated, the method proceeds to step 706, where electrosurgical energy is supplied to the first and second jaw members in accordance with a seal cycle algorithm or other suitable algorithm to seal the present, e.g., grasped, tissue between the jaw members. In various embodiments, the control device may emit, for example a tone, to signal that electrosurgical energy is being supplied to the first and second jaw members.

Next, at step 708, the control device determines if the seal cycle is complete. In various embodiments, if the control device determines that the seal cycle is not complete (due to an incomplete seal or disengagement of the first and/or second activation switch, for example), the control device emits a fault tone. In various embodiments, the control device displays on the display a fault condition. In various embodiments, if the seal cycle is determined to be complete and, thus, the tissue is sealed, the control device emits a success tone. In various embodiments, after the seal cycle is complete, the control device determines whether the activation mode has changed from first activation switch to the second activation switch.

If the control device determines at step 708 that the seal cycle is not complete, at step 710 the control device stops the supply of electrosurgical energy.

If the control device determines at step 708 that the seal cycle is complete, the method proceeds to step 720, where the control device determines if the first or second activation switch is still engaged. If the control device determines that the first activation switch is still engaged after completion of the seal cycle is complete, the method proceeds to step 718 where the control device activates a thermal cutting element in accordance with a first mode, e.g., a high temperature mode, where a suitable thermal cutting cycle or other suitable algorithm is utilized to supply thermal energy to the thermal cutting element for thermally cutting the previously sealed tissue grasped between the jaw members. At step 716, the control device determines if the thermal cutting cut cycle is complete and, if so, stops the supply of thermal energy at step 710. In various embodiments, the control device determines if the thermal cutting cycle is complete based on power consumption, temperature exceeding a predetermined threshold, and/or time exceeding a predetermined threshold.

If the control device determines at step 720 that the first activation switch is not engaged but the second activation switch is still engaged after completion of the seal cycle, the method proceeds to step 710 where the control device stops the supply of electrosurgical energy.

Returning to step 702, if the control device determines that tissue is not present between the first and second jaw members, the control device 1004 then proceeds to step 712 where the control device determines whether activation has been initiated by determining whether the first activation switch or that second activation switch is engaged.

If the control device determines that the first activation switch is engaged, then at step 718 a first thermal mode is activated, activating the thermal cutting element, e.g., in accordance with a high temperature mode of the thermal cutting cycle. If the control device determines that the second activation switch is engaged, then at step 714 a second thermal mode is activated, e.g., activating the thermal cutting element 150 in accordance with a low temperature mode of the thermal cutting cycle, wherein the thermal cutting element is heated to a lower temperature in the low temperature mode as compared to the high temperature mode. Other suitable modes are also contemplated.

Next at step 716, the control device determines if thermal cutting cycle is complete similarly as detailed above and, if complete, the control device stops the supply of thermal energy at step 710.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method, performed by a control device, for treating tissue, comprising:
    determining whether an activation switch has been engaged with tissue present between first and second jaw members;
    supplying electrosurgical energy to the first and second jaw members to seal the tissue present between the first and second jaw members in response to a determination that the activation switch has been engaged, wherein the electrosurgical energy is conducted between sealing surfaces of the first and second jaw members and through the tissue;
    determining if sealing is complete;
    stopping the supply of electrosurgical energy in response to a determination that sealing is complete;
    determining, in response to a determination that sealing is complete, whether the activation switch is still engaged;
    activating a cutting element to supply energy to cut the sealed tissue in response to a determination that the activation switch is still engaged;
    determining if cutting is complete; and
    stopping the supply of energy in response to a determination that the cutting is complete.

2. The method of claim 1, wherein activating the cutting element includes activating the cutting element in a high temperature mode, and wherein the method further includes:
    activating the cutting element in a low temperature mode in response to a determination that the activation switch is not still engaged and that a subsequent activation is initiated.

3. The method of claim 1, further including:
    activating the cutting element to supply energy to tissue to cut the tissue in response to a determination that the activation switch has been engaged without tissue present between the first and second jaw members.

4. The method of claim 3, wherein:
    the cutting element is activated in a different mode to supply energy to tissue to cut the tissue when the activation switch is engaged without tissue present between the first and second jaw members as compared to a mode wherein the cutting element is activated to supply energy to cut the sealed tissue.

5. The method of claim 1, further including:
    determining whether tissue is present between the first and second jaw members; and
    displaying on a display an indication that tissue is present in response to a determination that tissue is present between the first and second jaw members.

6. The method of claim 5, further including:
    displaying on a display an indication that tissue is not present in response to a determination that tissue is not present between the first and second jaw members.

7. The method of claim 1, further including:
    emitting a fault tone in response to a determination that the sealing is not complete.

8. The method of claim 7, further including:
    displaying on a display a fault condition.

9. The method of claim 1, further including:
    emitting a success tone in response to a determination that the sealing is complete.

10. The method of claim 1, wherein determining whether the activation switch has been engaged with tissue present between the first and second jaw members includes sensing impedance between the first and second jaw members.

11. A system for treating tissue, comprising:
    a surgical instrument including first and second jaw members configured to treat tissue, at least one of the first or second jaw members including an energizable cutting element, each of the first and second jaw members including a sealing surface;
    at least one processor; and
    at least one memory coupled to the at least one processor, the at least one memory having instructions stored thereon which, when executed by the at least one processor, cause the system to:
    determine whether an activation switch has been engaged with tissue present between the first and second jaw members;

supply electrosurgical energy to the first and second jaw members to seal the tissue present between the first and second jaw members, in response to a determination that the activation switch has been engaged, wherein the electrosurgical energy is conducted between sealing surfaces of the first and second jaw members and through the tissue;

determine if the sealing is complete;

stop the supply of electrosurgical energy in response to a determination that the sealing is complete;

determine, in response to a determination that sealing is complete, whether the activation switch is still engaged;

activate the cutting element to supply energy to cut the sealed tissue in response to a determination that the activation switch is still engaged;

determine if cutting is complete; and stop the supply of energy in response to a determination that the cutting is complete.

12. The system of claim 11, wherein activating the cutting element includes activating the cutting element in a high temperature mode, and wherein the instructions, when executed by the at least one processor, further cause the system to:

activate the cutting element in a low temperature mode in response to a determination that the activation switch is not still engaged and that a subsequent activation is initiated.

13. The system of claim 11, wherein the instructions, when executed by the at least one processor, further cause the system to:

activate the cutting element to supply energy to tissue to cut the tissue in response to a determination that the activation switch has been engaged without tissue present between the first and second jaw members.

14. The system of claim 13, wherein the instructions, when executed by the at least one processor, further cause the system to:

activate the cutting element in a different mode to supply energy to tissue to cut the tissue when the activation switch is engaged without tissue present between the first and second jaw members as compared to a mode wherein the cutting element is activated to supply energy to cut the sealed tissue.

15. The system of claim 11, wherein the instructions, when executed by the at least one processor, further cause the system to:

determine whether tissue is present between the first and second jaw members; and display on a display an indication that tissue is present, in response to a determination that tissue is present between the first and second jaw members.

16. The system of claim 15, wherein the instructions, when executed by the at least one processor, further cause the system to:

display on a display an indication that tissue is not present, in response to a determination that tissue is not present between the first and second jaw members.

17. The system of claim 11, wherein the instructions, when executed by the at least one processor, further cause the system to:

emit a fault tone in response to a determination that the sealing is not complete.

18. The system of claim 17, wherein the instructions, when executed by the at least one processor, further cause the system to:

display on a display a fault condition.

19. A non-transitory storage medium that stores a program causing a computer to execute a method for treating tissue, the method comprising:

determining whether an activation switch has been engaged with tissue present between first and second jaw members;

supplying electrosurgical energy to first and second jaw members to seal the tissue present between the first and second jaw members in response to a determination that the activation switch has been engaged with tissue present between first and second jaw members, wherein the electrosurgical energy is conducted between sealing surfaces of the first and second jaw members and through the tissue;

determining if sealing is complete;

stopping the supply of electrosurgical energy in response to a determination that sealing is complete;

determining, in response to a determination that sealing is complete, whether the activation switch is still engaged;

activating a cutting element of one of the first or second jaw members to supply energy to cut the sealed tissue in response to a determination that the activation switch is still engaged;

determining if cutting is complete; and stopping the supply of energy in response to a determination that the cutting is complete.

\* \* \* \* \*